United States Patent
Toth et al.

(10) Patent No.: US 6,990,172 B2
(45) Date of Patent: Jan. 24, 2006

(54) METHOD AND APPARATUS TO DETERMINE TUBE CURRENT MODULATION PROFILE FOR RADIOGRAPHIC IMAGING

(75) Inventors: Thomas L. Toth, Brookfield, WI (US); Steven J. Woloschek, Franklin, WI (US); Jonathan R. Schmidt, Wales, WI (US)

(73) Assignee: General Electric Company, Schenectady, NY (US)

( * ) Notice: Subject to any disclaimer, the term of this patent is extended or adjusted under 35 U.S.C. 154(b) by 36 days.

(21) Appl. No.: 10/782,485

(22) Filed: Feb. 19, 2004

(65) Prior Publication Data

US 2005/0185759 A1     Aug. 25, 2005

(51) Int. Cl.
*H05G 1/34* (2006.01)
(52) U.S. Cl. .......................... 378/16; 378/109
(58) Field of Classification Search ................. 378/16, 378/109, 110, 8, 108
See application file for complete search history.

(56) References Cited

U.S. PATENT DOCUMENTS

| | | |
|---|---|---|
| 5,379,333 A | 1/1995 | Toth |
| 5,450,462 A | 9/1995 | Toth et al. |
| 5,696,807 A | 12/1997 | Hsieh |
| 5,764,721 A | 6/1998 | Light et al. |
| 5,822,393 A | 10/1998 | Popescu |
| 5,867,555 A | 2/1999 | Popescu et al. |
| 6,067,341 A | 5/2000 | Horiuchi |
| 6,115,448 A * | 9/2000 | Hoffman .................... 378/19 |
| 2003/0185343 A1 | 10/2003 | Horiuchi |

FOREIGN PATENT DOCUMENTS

| | | |
|---|---|---|
| JP | 11-104121 | 4/1999 |
| JP | 2002253546 | 9/2002 |
| WO | WO-03/022019 A2 | 3/2003 |

* cited by examiner

*Primary Examiner*—Edward J. Glick
*Assistant Examiner*—Chih-Cheng Glen Kao
(74) *Attorney, Agent, or Firm*—Ziolkowski Patent Solutions Group, SC; Michael A. Della Penna; Carl B. Horton

(57) ABSTRACT

A method and apparatus is disclosed to acquire scout scan data of a subject and analyzed to determine a peak-to-peak modulation amplitude of a normalized waveform indicative of subject size and shape. The scout scan data provides a representation of patient size and shape that is associated with an ideal tube current modulation waveform or profile. The ideal tube current modulation profile may then be sampled or approximated at various points to determine a tube current modulation profile for implementation to acquire CT data with reduced dose but without sacrificing image quality.

21 Claims, 6 Drawing Sheets

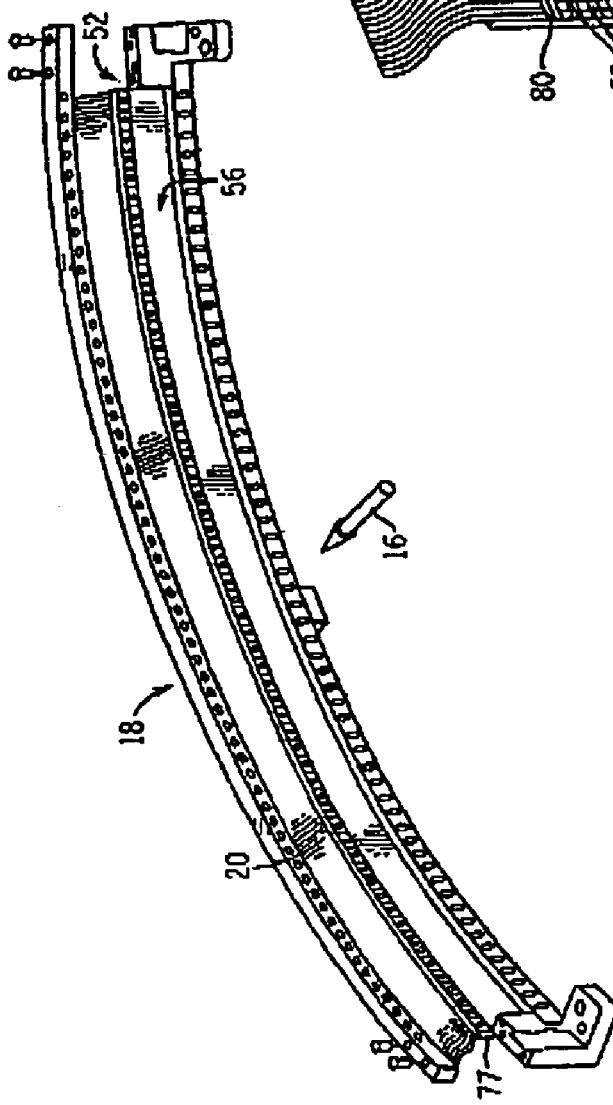
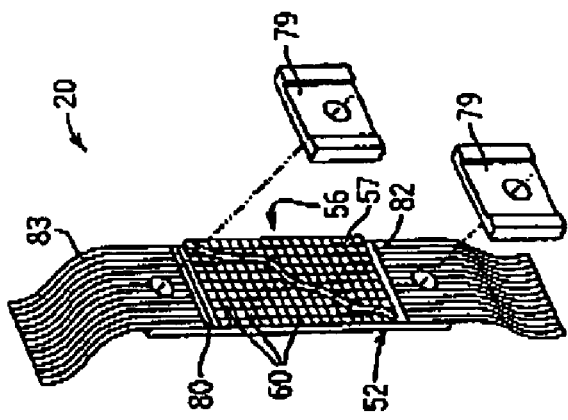
FIG. 3
FIG. 4

METHOD AND APPARATUS TO DETERMINE TUBE CURRENT MODULATION PROFILE FOR RADIOGRAPHIC IMAGING

BACKGROUND OF THE INVENTION

The present invention relates generally to diagnostic imaging and, more particularly, to a method and apparatus of tube current modulation for radiographic imaging, e.g. computed tomography (CT).

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray- detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

As described above, CT imaging is an imaging modality predicated upon the projection of radiographic imaging, e.g. x-rays, and reconstructing an image of the subject based on the subject's attenuation of the projected x-rays. Generally, driving an x-ray source at higher current levels produces images with less noise. On the other hand, extremely low x-ray tube current levels can cause severe artifacts in the reconstructed image. X-ray tube current may be characterized as being directly related to the amount of radiographic energy received by the subject, i.e. patient dose. As such, as x-ray tube current increases, so does the radiation dose received by the subject. While higher x-ray tube current levels result in less noisy images, higher tube current levels expose the subject to increased x-ray dose. Therefore, in establishing an imaging protocol for a given subject, a trade-off must be made between tube current and subject dose. Ideally, it is preferred to use the minimum radiation dose necessary to generate a diagnostically valuable image.

A number of techniques have been developed to determine a tube current modulation profile that achieves the two desire objectives: (1) diagnostically valuable images; and (2) minimum radiation exposure to the subject. A number of these techniques are predicted upon the acquisition and analysis of scout scan data to shape a tube current modulation profile that satisfies the above objectives. Notwithstanding the advancements achieved by these known imaging techniques, it has been shown that over-exposure as well as under-exposure of radiation can still be problematic and therefore expose the subject to unnecessary radiation or result in a noisy image that therefore requires re-scanning of the subject.

A number of tube current modulation techniques have been developed to enhance waveform shaping and x-ray generation using projection data from one or more scout scans. These techniques assume that the tube current modulation profile is symmetrical throughout a single gantry rotation cycle. It has been shown, however, that the ideal tube current modulation waveform may not be symmetrical. That is, these known techniques to determine tube current modulation fail to account for the asymmetry of the ideal modulating waveform. This asymmetry results in the subject being over-exposed or under-exposed to radiation depending upon the diagnostic objectives of the scan.

It would therefore be desirable to design a method and apparatus for tube current modulation that accounts for the asymmetry of an ideal tube current modulating profile.

BRIEF DESCRIPTION OF THE INVENTION

The present invention relates directly to a method and apparatus for tube current modulation that overcomes the aforementioned drawbacks.

Scout scan data is acquired of a subject and analyzed to determine a peak-to-peak modulation amplitude of a normalized waveform indicative of subject size and shape. The scout scan data provides a representation of patient size and shape such that an ideal tube current modulation waveform or profile may be developed. The ideal tube current modulation profile may then be sampled or approximated at various points to determine a tube current modulation profile for implementation. The differences between the tube current modulation profile for implementation and the ideal tube current modulation profile are reduced as the number of sampling points is increased.

Therefore, in accordance with one aspect of the present invention, a method of tube current modulation for radiographic data acquisition is provided. The method includes identifying a plurality of modulation points on a waveform indicative of at least one of subject size and subject shape, and determining a modulation factor at the plurality of the modulation points. The method further includes generating a modulation tube current waveform that substantially approximates the waveform indicative of at least one of subject size and subject shape based on a modulation factor at the plurality of modulation points.

According to another aspect of the present invention, a CT system is disclosed. The CT system includes a rotatable gantry having an opening to receive a subject to be scanned and a high frequency electromagnetic energy projection source configured to project a high frequency electromagnetic energy beam towards the subject. A scintillator array having a plurality of scintillator cells is also provided such that each cell is configured to detect high frequency electromagnetic energy passing through the subject. The CT system further includes a photodiode array optically coupled to the scintillator array and comprising a plurality of photodiodes to detect light output from a corresponding scintillator. A data acquisition system (DAS) is provided and connected to the photodiode array and configured to receive photodiode outputs. The CT system further includes an image reconstructor connected to the DAS and configured to reconstruct an image of the subject from the photodiode outputs received by the DAS. The CT system further includes a computer programmed to determine an ideal tube current modulation waveform to control projection of high frequency electromagnetic energy by the high frequency electromagnetic projection source for CT data acquisition of the subject. The computer is further programmed to evaluate the ideal tube current modulation waveform at a plurality of magnitudes and determine an approximate tube current modulation waveform from the plurality of magnitudes.

In accordance of with another aspect of the present invention, a computer readable storage medium having a computer program stored thereon is provided. The computer program represents a set of instructions that while executed by a computer causes the computer to command a radiographic data acquisition system to carry out a scout scan to acquire pre-scan data indicative of subject size and subject shape. The computer is also caused to determine a first tube current modulation waveform ideal for the subject size and subject shape from the pre-scan data. The set of instructions further causes the computer to evaluate a portion of the first tube current modulation waveform corresponding to 90 degrees of gantry rotation and determine a second tube current modulation waveform that approximates the first tube current modulation waveform from the portion of the first modulation waveform.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 3 is a perspective view of one embodiment of a CT system detector array.

FIG. 4 is a perspective view of one embodiment of a detector.

DETAILED DESCRIPTION OF THE PREFERRED EMBODIMENT

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
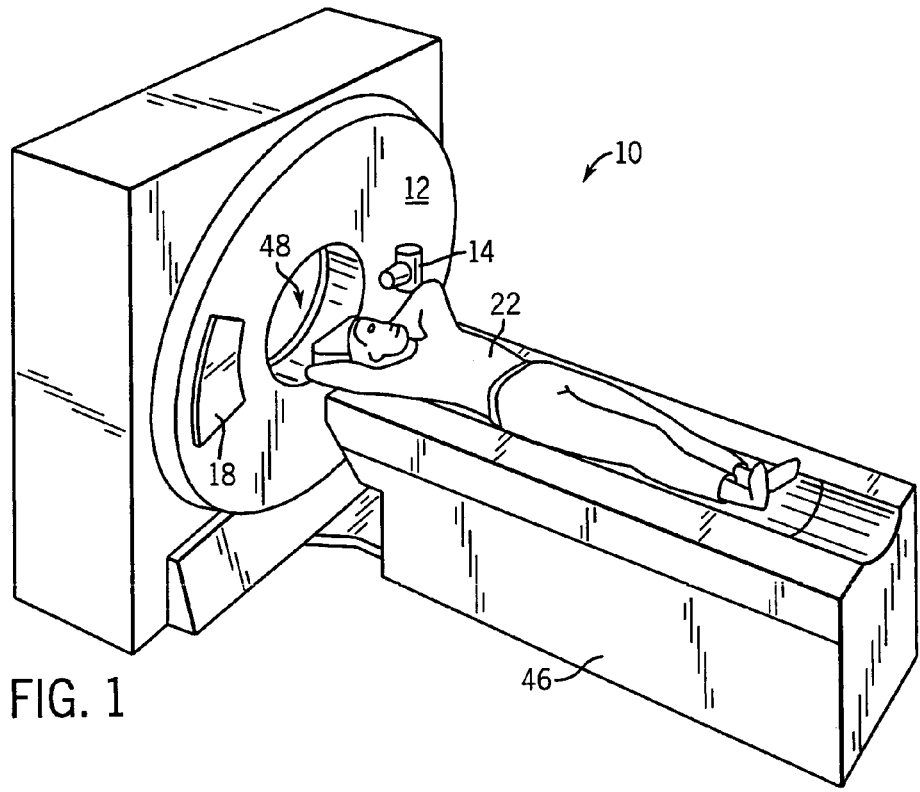
FIG. 1 is a pictorial view of a CT imaging system.
Figure 2:
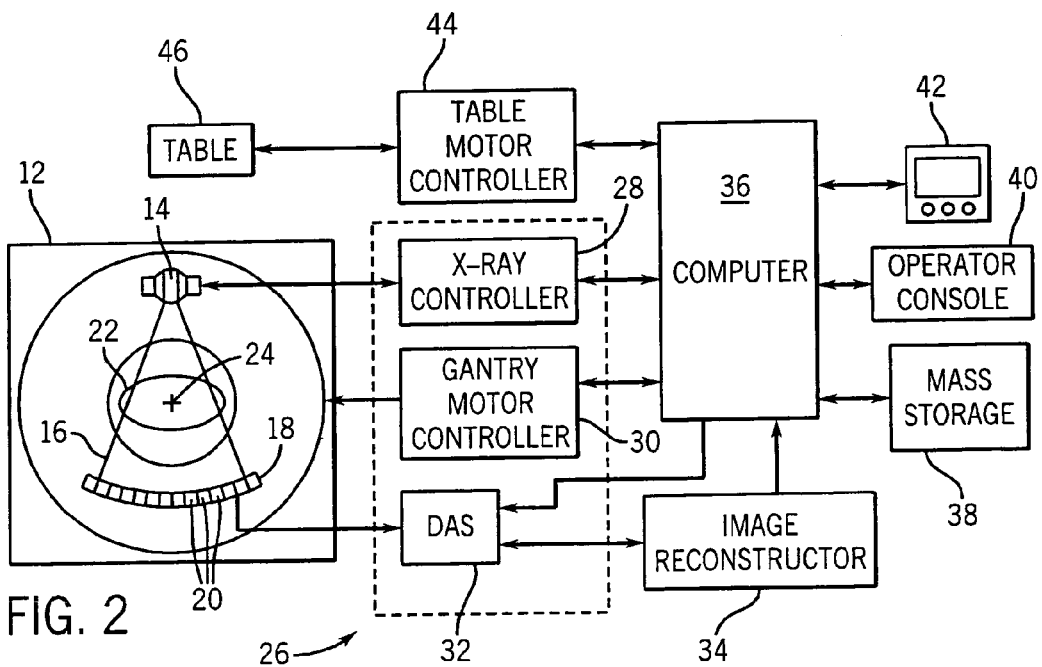
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

As shown in FIGS. 3 and 4, detector array 18 includes a plurality of scintillators 57 forming a scintillator array 56. A collimator (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 83. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
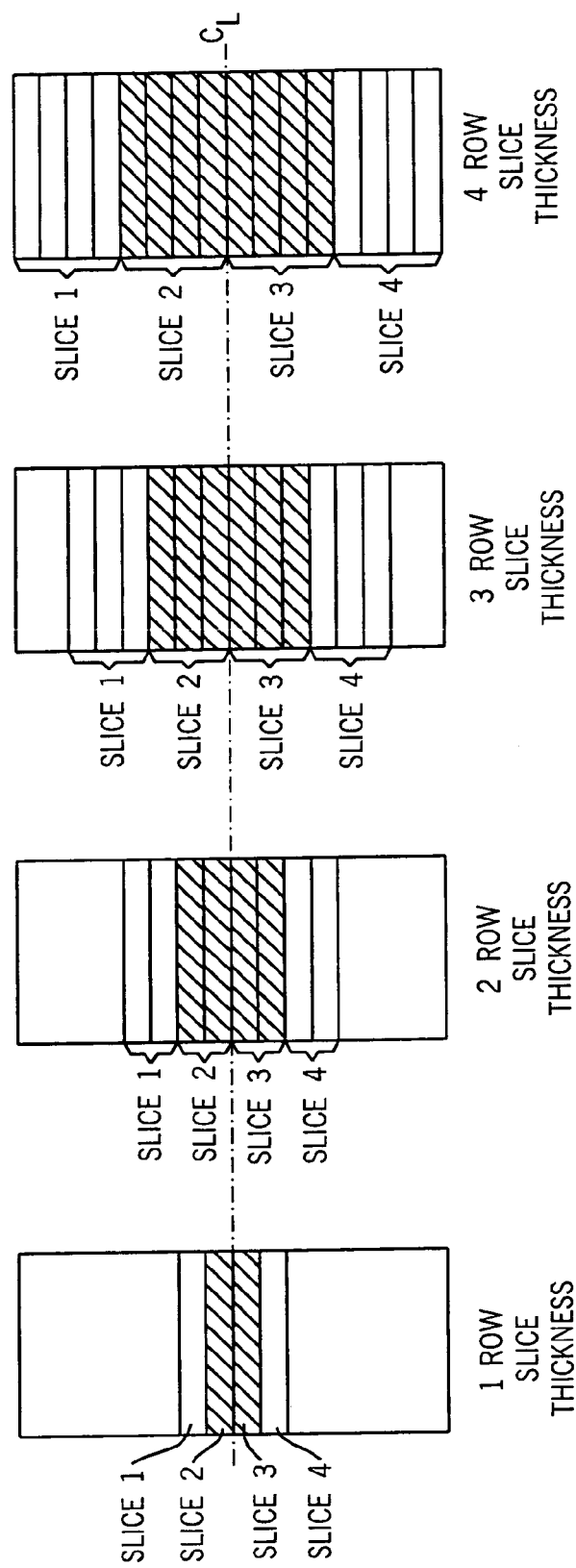
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected about line $C_L$ from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

The present invention is directed to a method and apparatus of determining a tube current modulation waveform profile that is tailored to a specific subject to reduce subject exposure to radiation without sacrificing image quality. By generating an ideal tube current modulation profile for a range of subjects to be encountered and analyzing points along that profile, the present invention is able to develop and cause generation of x-rays consistent with a radiation dose profile that substantially approximates the ideal profile for the given subject. The present invention analyzes data acquired during a CT scan or computer modeling to represent a model of the subject as an ellipse. Through experimentation and computer modeling using fundamental x-ray physics equations it can be shown that the ideal tube current modulation waveform has a shape or profile that is a function of an elliptical subject model. Specifically, the ideal tube current modulation waveform is a function of a small axis diameter and oval ratio of the subject. The oval ratio and the small axis diameter are preferably determined from a pair of scouts. It contemplated however that additional techniques in addition to using scout projections may be use to determine a model of the subject.

Figure 6:
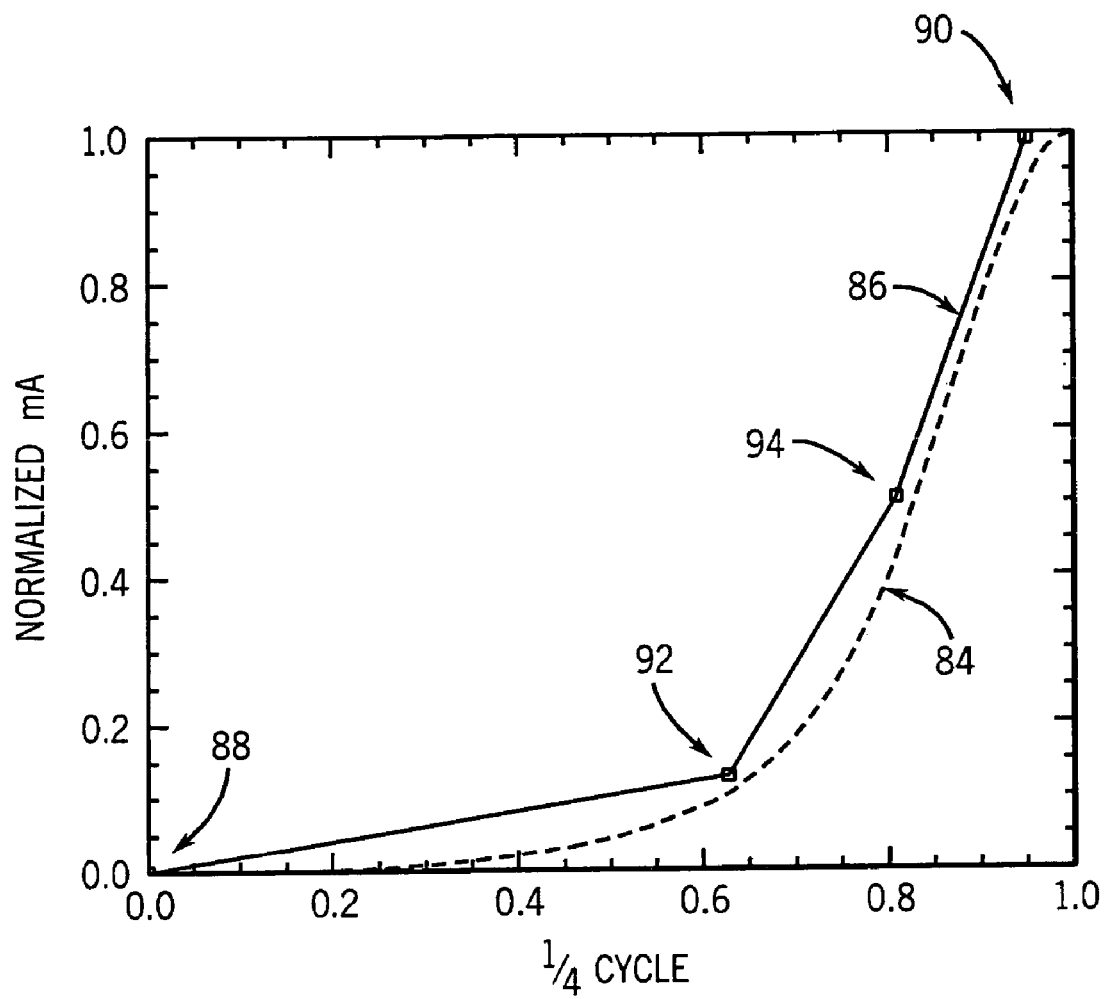
FIG. 6 is a pair of waveforms illustrating an ideal tube current modulation waveform based on subject shape and subject size and a tube current modulation waveform for implementation that approximates the ideal tube current modulation waveform in accordance with the present invention.

Referring now to FIG. 6, a normalized ideal current waveform or profile 84 is shown for a specific elliptical case relative to an approximated tube current modulation waveform 86 that will be used to define x-ray generation by a high frequency electromagnetic energy projection source for CT data acquisition. Waveform 84 is normalized along two dimensions. First, the waveform is normalized to a peak-to-peak modulation amplitude or, in other words, a high tube current set to a value of one and low tube current set to a value of zero. The waveform is also normalized to a one quarter modulation cycle, i.e. 90 degrees of gantry rotation is set to a value of one. The normalized waveform is generated for a set of elliptical cases over the range of subjects to be scanned. More particularly, each waveform is indicative of subject shape and size as defined by small axis diameter and oval ratio data acquired from the subject during the scout scans. As will be described, the normalized waveform may be analyzed to determine an approximate tube current modulation waveform 86 that is used during CT data acquisition.

For example, the ideal tube current modulation waveform 84 may be sampled at a number of points and evaluated thereat to determine the approximate tube current modulation waveform 86. In the example illustrated in FIG. 6, four points 88–94 are evaluated. Specifically, the magnitude at 88 corresponds to the lowest tube current modulation value which, in FIG. 6, corresponds to the origin of the curves. The magnitude at 90, in contrast, corresponds to the normalized maximum tube current value. While it is contemplated that the minimum and maximum normalized tube current values can be used to approximate the ideal tube current modulation waveform, it is preferred that additional points along the ideal waveform 84 be evaluated.

As shown in FIG. 6, the magnitude at 92 corresponds to ten percent of peak-to-peak modulation. In addition to evaluating the waveform 84 at ten percent of peak-to-peak modulation, in illustrated example, the point corresponding to fifty percent of peak-to-peak modulation magnitude is also evaluated at 94 . From these values or modulation factors 88–94, a linear or piece-wise approximation of the ideal tube current modulation waveform may be determined and used to control the high frequency of electromagnetic energy projection source. One skilled in the art will appreciate that to further approximate the ideal tube current modulation waveform 84, additional modulation points or magnitude (e.g. ninety percent of peak-to-peak modulation amplitude) may be evaluated.

Figure 7:
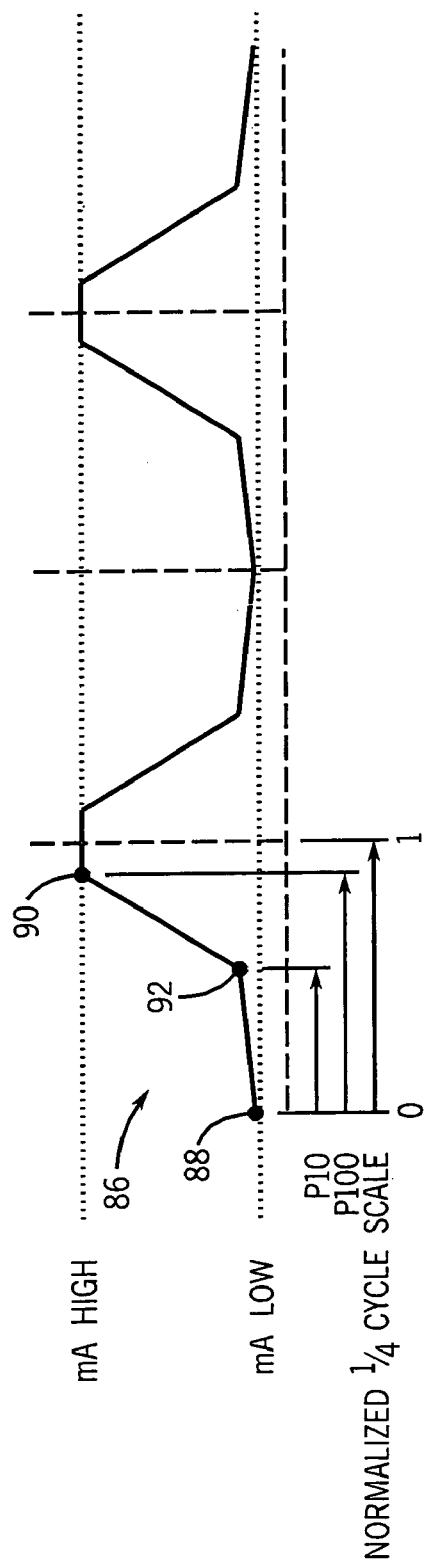
FIG. 7 is a tube current modulation profile in accordance with the present invention.

Referring now to FIG. 7, a tube current modulation waveform generated from using a polynomial expression for the evaluated points of an ideal tube current modulation waveform is shown. The tube current modulation waveform 86 illustrated in FIG. 7 is based on a three point approximation of an ideal tube current modulation waveform. In this regard, the magnitude at 92, which corresponds to ten percent of peak-to-peak modulation amplitude, is evaluated and fitted to a polynomial expression that is a function of small axis diameter (projection measure) determined from one or more scout scans. The magnitude at 92 corresponds to ten percent of the peak-to-peak modulation amplitude and it can be defined by the following equation:

$$P10 = a_0 + a_1 O + a_2 D + a_3 OD + a_4 O^2 + a_5 D^2 + a_6 O^2 D + a_7 OD^2 + a_8 D^3 \quad \text{Eqn. 1.}$$

| Eq coeff | Variable |
|---|---|
| $a_0$ | constant |
| $a_1$ | oval ratio (ovr) |
| $a_2$ | small axis diam (diam) |
| $a_3$ | ovr * diam |
| $a_4$ | ovr$^2$ |
| $a_5$ | diam$^2$ |
| $a_6$ | ovr$^2$ * diam |
| $a_7$ | diam$^2$ * ovr |
| $a_8$ | diam$^3$ |

Further, the modulation factor at 90 which corresponds to 100 percent of the peak-to-peak modulation amplitude may be defined by:

$$P100 = b_0 + b_1 O + b_2 D + b_3 OD + b_4 O^2 + b_5 D^2 + b_6 O^2 D + b_7 OD^2 + b_8 D^3 \quad \text{Eqn. 2;}$$

| Eq coeff | Variable |
|---|---|
| $b_0$ | constant |
| $b_1$ | oval ratio (ovr) |
| $b_2$ | small axis diam (diam) |
| $b_3$ | ovr * diam |
| $b_4$ | $ovr^2$ |
| $b_5$ | $diam^2$ |
| $b_6$ | $ovr^2$ * diam |
| $b_7$ | $diam^2$ * ovr |
| $b_8$ | $diam^3$ |

In addition, to avoid over-exposure or under-exposure, it is contemplated that an error margin may be used to offset the values determined at the evaluated modulation points. For example, in one embodiment, die calculated or determined values are temporally (in x) offset by a negative amount or in magnitude (in y) by a positive amount. A value of adjustment is 0.02 and is applied in (y) where the waveform slope at the particular modulation point is less than one and is applied in (x) when the waveform slope at a particular modulation point is greater than one. The high frequency electromagnetic energy projection source will be commanded to generate x-rays or other radiographic energy in a matter as defined by the tube current modulation waveform 86 that is a linear approximation of the ideal tube current modulation waveform.

It is also contemplated that the approximate cube current modulation waveform may be determined by characterizing the low tube current flat region of the ideal waveform with a single reference point, e.g. ten percent of peak-to-peak modulation, and the remainder of the waveform with a polynomial expression of appropriate degree e.g. a four point function. The polynomial expression may be fitted as a function of minimum diameter and oval ratio in a manner similar to that described above with respect to piecewise approximation. Additionally, other functions may be used such as an appropriate sinusoidal, elliptical, circular, parabolic or other appropriate analytic continuous function for which the parameters arc fitted as a function of minimum diameter and/or oval ratio.

The technique described above is designed to reduce overall tube use and radiation exposure to a subject without sacrificing image quality. The above technique is also applied with individualized scan protocols such that the physical variations of a scan population are taken into account with each scan. It is contemplated however that various waveforms may be developed to account for variations in scan population and stored in an accessible database. During scanner operation, the oval ratio and diameter of the patient are estimated from scout scans and functions or relationships such as those defined above by equations 1 and 2 are used to generate the appropriate tube current modulation profile for controlling x-ray generation for CT data acquisition for the patient. One skilled in the art will appreciate that other functions or equations other than those specifically identified above may be used to generate the appropriate tube current modulation profile.

Figure 8:
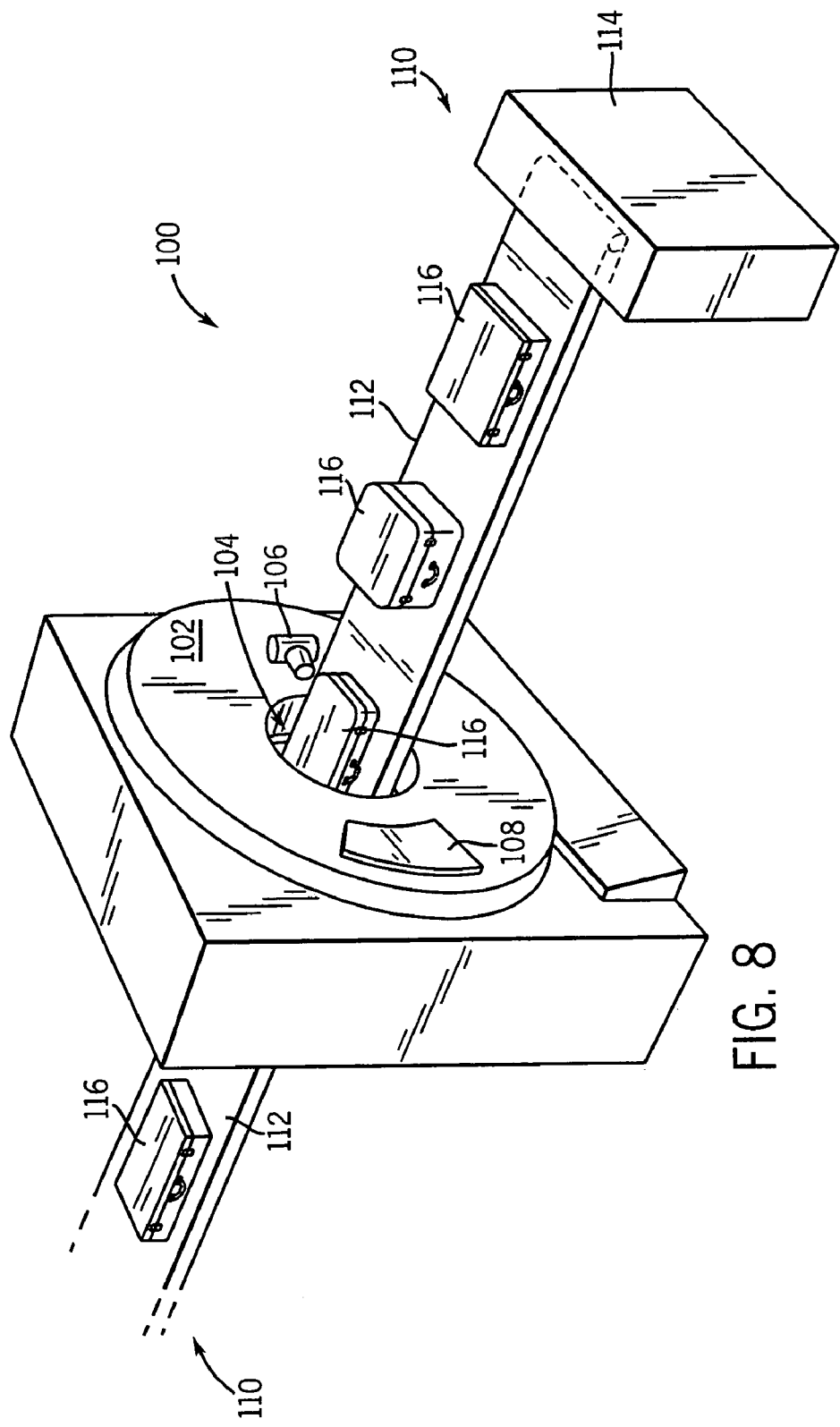
FIG. 8 is a pictorial view of a CT system for use with a non-invasive package inspection system.

Referring now to FIG. 8, package/baggage inspection system 100 includes a rotatable gantry 102 having an opening 104 therein through which packages or pieces of baggage may pass. The rotatable gantry 102 houses a high frequency electromagnetic energy source 106 as well as a detector assembly 108. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc. the system 100 includes a computer capable of carrying out the technique heretofore described.

The present invention has been described with respect to an imaging technique for optimizing radiation dose during CT data acquisition that determines ideal modulation waveforms as a function of projection angle for a set of phantoms. It is understood that the set of phantoms may be scanned and the ideal modulation waveforms may be determined from axial attenuation data. Coefficients at modulation points along the ideal modulation waveforms are determined and capture or represent the relationship between the size and shape of a phantom and an appropriate modulation waveform shape. As such, when scanning a subject, a scout scan, taken at a fixed angle of zero and/or ninety degrees, is used to determine a projection area and projection measure. From the determined coefficients as well as the projection area and projection measure, an appropriate tube current modulation waveform to use for a specific subject to optimize radiation dose may be determined as a function of z-axis subject position and gantry angle during scanning.

Therefore, in accordance with one embodiment of the present invention, a method of tube current modulation for radiographic data acquisition is provided. The method includes identifying a plurality of modulation points on a waveform indicative of at least one of subject size and subject shape, and determining a modulation factor at the plurality of the modulation points. The method further includes generating a modulation tube current waveform that substantially approximates the waveform indicative of at least one of subject size and subject shape based on a modulation factor at the plurality of modulation points.

According to another embodiment of the present invention, a CT system is disclosed. The CT system includes a rotatable gantry having an opening to receive a subject to be scanned and a high frequency electromagnetic energy projection source configured to project a high frequency electromagnetic energy beam towards the subject. A scintillator array having a plurality of scintillator cells is also provided such that each cell is configured to detect high frequency electromagnetic energy passing through the subject. The CT system further includes a photodiode array optically coupled to the scintillator array and comprising a plurality of photodiodes to detect light output from a corresponding scintillator. A data acquisition system (DAS) is provided and connected to the photodiode array and configured to receive photodiode outputs. The CT system further includes an image reconstructor connected to the DAS and configured to reconstruct an image of the subject from the photodiode outputs received by the DAS. The CT system further includes a computer programmed to determine an ideal tube current modulation waveform to control projection of high frequency electromagnetic energy by the high frequency electromagnetic projection source for CT data acquisition of the subject. The computer is further programmed to evaluate the ideal tube current modulation waveform at a plurality of magnitudes and determine an approximate tube current modulation waveform from the plurality of magnitudes.

In accordance of with another embodiment of the present invention, a computer readable storage medium having a computer program stored thereon is provided. The computer program represents a set of instructions that while executed by a computer causes the computer to command a radiographic data acquisition system to carry out a scout scan to acquire pre-scan data indicative of subject size and subject shape. The computer is also caused to determine a first tube current modulation waveform ideal for the subject size and subject shape from the pre-scan data. The set of instructions further causes the computer to evaluate a portion of the first tube current modulation waveform corresponding to 90 degrees of gantry rotation and determine a second tube current modulation waveform that approximates the first tube current modulation waveform from the portion of the first modulation waveform.

The present invention has been described in terms of the preferred embodiment, and it is recognized that equivalents, alternatives, and modifications, aside from those expressly stated, are possible and within the scope of the appending claims.

What is claimed is:

1. A method of tube current modulation for radiographic data acquisition, the method comprising the steps of:
   identifying a plurality of modulation points on a waveform indicative of at least one of subject size and subject shape;
   determining a modulation factor at the plurality of modulation points; and
   generating a modulation tube current waveform that substantially approximates the waveform indicative of at least one of subject size and subject shape based on a modulation factor at the plurality of modulation points.

2. The method of claim 1 further comprising the step of carrying out a scout scan of a subject to determine the waveform indicative of at least one of subject size and subject shape.

3. The method of claim 1 wherein the step of identifying includes the step of inspecting one-half of a modulating cycle.

4. The method of claim 1 further comprising the step of modifying each modulation factor by an error value that is dependent upon a slope of the waveform at a respective modulation point.

5. The method of claim 4 further comprising the step of increasing the modulation factor as a function of time if the slope at a respective modulation point is greater than 1.0 and increasing the modulation factor as a function of magnitude if the slope at a respective modulation point is less than 1.0.

6. The method of claim 1 wherein the plurality of modulation points include points at ten percent, ninety percent, and one-hundred percent of waveform magnitude.

7. The method of claim 1 further comprising the step of determining the modulation factor of each modulation point based on a polynomial expression of subject size and subject shape at each modulation point.

8. The method of claim 1 further comprising the step of generating the modulation tube current waveform based on changes in oval ratio and diameter of a subject during acquisition of scout scan data.

9. A CT system comprising:
   a gantry having an opening to receive a subject to be scanned;
   a high frequency electromagnetic energy projection source configured to project a high frequency electromagnetic energy beam toward the subject;
   a scintillator array having a plurality of scintillator cells, wherein each cell is configured to detect high frequency electromagnetic energy passing through the subject;
   a photodiode array optically coupled to the scintillator array and comprising a plurality of photodiodes configured to detect light output from a corresponding scintillator cell;
   a data acquisition system (DAS) connected to the photodiode my and configured to receive photodiode outputs;
   an image reconstructor connected to the DAS and configured to reconstruct an image of the subject from the photodiode outputs received by the DAS; and
   a computer programmed to:
      determine an ideal tube current modulation waveform to control projection of high frequency electromagnetic energy by the high frequency electromagnetic energy projection source for CT data acquisition from the subject;
      evaluate the ideal tube current modulation waveform at a plurality of magnitudes;
      generate at least one polynomial expression fit to values evaluated at the plurality of magnitudes; and
      determine an approximate tube current modulation waveform from the at least one polynomial expression.

10. The CT system of claim 9 wherein the computer is further programmed to control the high frequency electromagnetic energy projection source such that high frequency electromagnetic energy projection toward the subject conforms to the approximate tube current modulation waveform.

11. The CT system of claim 9 wherein the computer is further programmed to determine the ideal tube current modulation waveform from a scout scan.

12. The CT system of claim 11 wherein the computer is further programmed to carry out the scout scan to determine a size and a shape of the subject.

13. The CT system of claim 12 wherein the computer is further programmed to determine the size and the shape from data acquired in one-quarter of gantry rotation.

14. The CT system of claim 13 wherein the ideal tube current modulation waveform is a function of oval ratio and minimum subject diameter during a one-quarter quarter gantry rotation cycle.

15. The CT system of claim 9 wherein the plurality of magnitudes includes three separate magnitudes on a normalized ideal tube current modulation waveform.

16. The CT system of claim 15 wherein the three magnitudes correspond to values at 10 percent, 90 percent, and 100 percent of peak waveform magnitude.

17. The CT system of claim 15 wherein the computer is further programmed to increase in number the plurality of magnitudes that are evaluated to reduce differences between the ideal tube current modulation waveform and the approximate tube current modulation waveform.

18. A computer readable storage medium having a computer program stored thereon and representing a set of instructions that when executed by a computer causes a computer to:
   command a radiographic data acquisition system to carry out a scout scan to acquire pre-scan data indicative of subject size and subject shape;
   determine a first tube current modulation waveform ideal for the subject size and the subject shape front the pre-scan data;
   evaluate a portion of the first tube current modulation waveform corresponding to ninety degrees of gantry rotation; and determine a second tube current modulation waveform that approximates the first tube current modulation waveform from a polynomial fit of the evaluated portion of the first modulation waveform.

19. The computer readable storage medium of claim 18 wherein the set of instructions further causes the computer to normalize the portion of the first tube current modulation waveform to a peak magnitude of one and determine the second tube current modulation waveform by evaluating more then two points along the normalized portion of the first modulation waveform.

20. The computer readable storage medium of claim 19 wherein the set of instructions further causes the computer to control an x-ray source to project x-rays toward a subject based on the second tube current modulation waveform.

21. A CT system comprising:
  a gantry having an opening to receive a subject to be scanned;
  a high frequency electromagnetic energy projection source configured to project a high frequency electromagnetic energy beam toward the subject;
  a scintillator array having a plurality of scintillator cells, wherein each cell is configured to detect high frequency electromagnetic energy passing through the subject;
  a photodiode ray optically coupled to the scintillator array and comprising a plurality of photodiodes configured to detect light output from a corresponding scintillator cell;
  a data acquisition system (DAS) connected to the photodiode array and configured to receive photodiode outputs;
  an image reconstructor connected to the DAS and configured to reconstruct an image of the subject from the photodiode outputs received by the DAS; and
  a computer programmed to:
    determine an ideal tube current modulation waveform from a scout scan to control projection of high frequency electromagnetic energy by the high frequency electromagnetic energy projection source for CT data acquisition from the subject wherein the ideal tube current modulation waveform is a function of oval ratio and minimum subject diameter during a one-quarter gantry rotation cycle;
    determine a size and a shape of the subject from the scout scan;
    determine the size and the shape from data acquired in one-quarter of gantry rotation;
    evaluate the ideal tube current modulation waveform at a plurality of magnitudes; and
    determine an approximate tube current modulation waveform from values at the plurality of magnitudes.

* * * * *

UNITED STATES PATENT AND TRADEMARK OFFICE
CERTIFICATE OF CORRECTION

PATENT NO.   : 6,990,172 B2
DATED        : January 24, 2006
INVENTOR(S)  : Toth et al.

It is certified that error appears in the above-identified patent and that said Letters Patent is hereby corrected as shown below:

Column 10,
Line 6, delete "my" and insert -- array --;
Line 41, delete "quarter" (second occurrence);
Line 62, delete "front" and insert -- from --;

Column 11,
Line 25, delete "ray" and insert -- array --.

Signed and Sealed this

Eleventh Day of April, 2006

JON W. DUDAS
*Director of the United States Patent and Trademark Office*